United States Patent
Iwasaki

[11] Patent Number: 6,060,623
[45] Date of Patent: May 9, 2000

[54] PROCESS FOR PRODUCING AMINE BORANE COMPOUND

[75] Inventor: Yoshiaki Iwasaki, Ichikawa, Japan

[73] Assignee: Shiroi Yakuhin Co., Ltd., Japan

[21] Appl. No.: 09/287,525

[22] Filed: Apr. 7, 1999

[30] Foreign Application Priority Data

Jan. 8, 1999 [JP] Japan .................................. 11-002629

[51] Int. Cl.[7] ....................................................... C07F 5/02
[52] U.S. Cl. .................................................................. 564/8
[58] Field of Search ...................................... 564/8

[56] References Cited

U.S. PATENT DOCUMENTS 5,565,615 10/1996 Holzner et al. ............................. 564/8

FOREIGN PATENT DOCUMENTS 0 832 894  4/1998  European Pat. Off. .
158792   12/1981  Japan .
109991    4/1998  Japan .

OTHER PUBLICATIONS

Brown, Herbert C. et al., "Molecular Addition Compounds. 9. Effect of Structure on the Reactivities of Representative Borane–Amine Complexes in Typical Reactions Such as Hydrolysis, Hydroboration, and Reduction", Inorganic Chemistry, Vol. 23, No. 18, 1984, pp. 2746–2753.

*Primary Examiner*—Peter O'Sullivan
*Attorney, Agent, or Firm*—Webb Ziesenheim Logsdon Orkin & Hanson, P.C.

[57] ABSTRACT

A process for producing an amine borane compound, comprising the steps of:
- reacting an amine salt with sodium borohydride in an organic solvent,
- distilling off the organic solvent to thereby obtain a distillation residue,
- adding an aqueous alkali hydroxide solution to the distillation residue to thereby form an organic phase and a water phase,
- fractionating the organic phase, and
- distilling off the organic solvent from the organic phase. This process is advantageous in terms of cost and ensures safe work environment because the aqueous alkali hydroxide solution is used in place of an organic solvent in the purification (recrystallization) of the amine borane compound. Moreover, the decomposition of the amine borane compound is suppressed by the addition of the aqueous alkali hydroxide solution.

4 Claims, No Drawings

PROCESS FOR PRODUCING AMINE BORANE COMPOUND

FIELD OF THE INVENTION

The present invention relates to a process for producing an amine borane compound. More particularly, the present invention relates to a process for producing an amine borane compound having high purity.

BACKGROUND OF THE INVENTION

The amine borane compound such as trihydro(N-methylmethanamine)boron represented by the formula $(CH_3)_2NH:BH_3$ or (N,N-dimethylmethanamine) trihydroboron represented by the formula $(CH_3)_3N:BH_3$ finds a wide variety of uses as an industrial reagent. For example, the amine borane compound is used as a reducing agent in the plating, photographic development and production of printed circuit boards.

The above amine borane compound is commonly produced by reacting an amine salt with sodium borohydride of the formula $NaBH_4$. However, the purity of the amine borane compound obtained by this reaction is not always high, so that, after the completion of the reaction, the amine borane compound must be purified by, for example, recrystallization.

For example, Japanese Patent Laid-open Publication No. 56(1981)-158792 discloses a process comprising reacting an amine salt with sodium borohydride in dimethoxyethane as a reaction solvent, distilling off dimethoxyethane as the reaction solvent from the obtained reaction mixture, dissolving the resultant distillation residue in an organic solvent such as benzene or dichloromethane, removing impurities by filtration and distilling off the solvent to thereby obtain a purified amine borane compound. However, in this process, a large amount of organic solvent such as benzene or dichloromethane is used in the purification with the result that high cost is incured and a problem of work environment is encountered. Furthermore, the yield and purity of the amine borane compound are not necessarily satisfactory, thereby leaving room for improvement.

Japanese Patent Laid-open Publication No. 10(1998) 109991 discloses a process in which the purification after the reaction comprises distilling off 1,2-dimethoxyethane as a reaction solvent from the obtained reaction mixture, adding water and a water insoluble organic extractant or the mixture thereof so that an organic phase and a water phase are formed, separating the organic phase from the water phase and distilling the organic phase to thereby obtain an amine borane compound. The organic extractant used in the process is an aromatic hydrocarbon, a halogenated hydrocarbon or the like, so that, as in the process of Japanese Patent Laid-open Publication No. 56(1981)-158792, room for improvement is left in terms of cost, work environment, product yield and product purity.

The present invention has been made in view of the above prior art. The object of the present invention is to provide a process for producing an amine borane compound, wherein the amine borane compound formed by the reaction of an amine salt and sodium borohydride can be purified to a high degree with low cost, safely and at a high yield.

SUMMARY OF THE INVENTION

The process for producing an amine borane compound having high purity according to the present invention comprises the steps of:

reacting an amine salt with sodium borohydride in an organic solvent, distilling off the organic solvent to thereby obtain a distillation residue, adding an aqueous alkali hydroxide solution to the distillation residue to thereby form an organic phase and a water phase, fractionating the organic phase, and distilling off the organic solvent from the organic phase.

In the present invention, it is preferred that the organic solvent be 1,2-dimethoxyethane and that the amine salt be a dimethylammonium salt or a trimethylammonium salt.

Further, preferably, the aqueous alkali hydroxide solution is an aqueous sodium hydroxide solution having a concentration (normality) of 0.1 to 12 N.

The process of the present invention is advantageous in terms of cost and ensures safe work environment because the aqueous alkali hydroxide solution is used in place of an organic solvent in the purification (recrystallization) of the amine borane compound. Moreover, the decomposition of the amine borane compound is suppressed by the addition of the aqueous alkali hydroxide solution so that the reaction mixture is rendered alkaline, thereby enabling obtaining the amine borane compound having high purity at a high yield.

DETAILED DESCRIPTION OF THE INVENTION

The present invention will now be further described in detail.

In the present invention, first, the amine borane compound is synthesized by the reaction of an amine salt and sodium borohydride.

The amine salt as the starting compound can appropriately be selected in conformity with the desired amine borane compound. For example, a dimethylamine salt is used as the amine salt in the production of trihydro(N-methylmethanamine)boron of the formula $(CH_3)_2NH:BH_3$. Although the form of the salt may be any of a hydrochloride, a sulfate, a nitrate and the like, it is preferred to be a hydrochloride. When the desired product is (N,N-dimethylmethanamine)trihydroboron of the formula $(CH_3)_3N:BH_3$, use is made of a trimethylamine salt, preferably, trimethylamine hydrochloride. Further, depending on the type of the desired amine borane compound, use can be made of diethylamine hydrochloride, dibutylamine hydrochloride, triethylamine hydrochloride, tributylamine hydrochloride, methylethylamine hydrochloride, dimethylethylamine hydrochloride, diethylmethylamine hydrochloride, etc. These amine salts may be used either individually or in combination.

Although the reaction of an amine salt and sodium borohydride is an equimolar reaction, it is preferred that sodium borohydride be used in a slight excess. It is especially preferred that about 1.0 to 1.1 mol of sodium borohydride be used per mol of the amine salt.

The reaction of an amine salt and sodium borohydride is performed in an organic solvent. Various organic solvents can be used without any particular limitation as long as any adverse influence is not exerted on the reaction. For example, use can be made of 1,2-dimethyloxyethane, tetrahydrofuran, dioxane, dimethylformamide and dimethoxyethane. Specifically, 1,2-dimethoxyethane is preferred.

The organic solvent is preferably used in an amount of 50 to 300 ml, still preferably 50 to 150 ml, and more preferably 70 to 120 ml per mol of the total of amine salt and sodium borohydride. Per mol of sodium borohydride, the organic solvent is preferably used in an amount of 100 to 600 ml, more preferably 100 to 300 ml, and most preferably 140 to 240 ml.

The reaction of an amine salt and sodium borohydride is preferably performed at −10 to 60° C., more preferably 0 to 40° C., and most preferably 5 to 30° C. Although the reaction time is appropriately set in conformity with the reactants, reaction temperature, etc., it is generally in the range of about 48 to 72 hr, preferably about 50 to 60 hr.

An amine borane compound is formed by the above reaction, and crude amine borane compound is obtained by distilling off the organic solvent. The crude amine borane compound contains impurities such as byproducts, unreacted compounds and solvent residue. Therefore, in the present invention, the crude amine borane compound is purified by the recrystallization method using an aqueous alkali hydroxide solution.

Examples of the aqueous alkali hydroxide solutions include an aqueous sodium hydroxide solution, an aqueous potassium hydroxide solution, an aqueous magnesium hydroxide solution, an aqueous calcium hydroxide solution, an aqueous aluminum hydroxide solution and suspensions thereof. Especially preferred use is made of an aqueous sodium hydroxide solution.

The concentration (normality) of the aqueous alkali hydroxide solution is preferably in the range of 0.1 to 12 N, more preferably 0.3 to 5 N, and most preferably 0.5 to 1.5 N.

The aqueous alkali hydroxide solution is preferably used in such an amount that the amount of alkali per mol of crude amine borane compound is in the range of 0.02 to 2.3 equivalents, still preferably 0.1 to 0.3 equivalent and that the amount of alkali per mol of sodium borohydride used in the production of crude amine borane compound is in the range of 0.02 to 2.3 equivalents, still preferably 0.1 to 0.3 equivalent.

The contact of the crude amine borane compound and the aqueous alkali hydroxide solution is preferably conducted at 0 to 50° C., still preferably 10 to 30° C.

When the aqueous alkali hydroxide solution is added to the crude amine borane compound and allowed to stand still, a separation occurs into a water phase and an organic phase. Unreacted compounds and by-products are absorbed into the water phase, while the organic phase is composed of the residual organic solvent and the amine borane compound. Thus, the organic phase is fractionated and filtered, and the residual organic solvent is distilled off. As a result, an amine borane compound having high purity is obtained.

The purity of the thus obtained amine borane compound is extremely high. The purity measurement by iodometry shows the production of an amine borane compound having a purity of at least 90%, preferably at least 95%, and more preferably at least 97%.

The addition of the alkali suppresses the decomposition of the amine borane compound, so that the yield is also extremely high. Generally, the amine borane compound is obtained at a yield of at least 80%.

As is apparent from the foregoing, the process of the present invention is advantageous in terms of cost and ensures a safe work environment because the aqueous alkali hydroxide solution is used in place of an organic solvent in the purification (recrystallization) of the amine borane compound. Moreover, the decomposition of the amine borane compound is suppressed by the addition of the aqueous alkali hydroxide solution so that the reaction mixture is rendered alkaline, thereby enabling the obtainment of the amine borane compound having high purity at a high yield.

EXAMPLE

The present invention will now be illustrated with reference to the following Examples, which in no way limit the scope of the invention.

Example 1

125 g (1.533 mol) of dimethylamine hydrochloride was suspended in 204 g of 1,2-dimethoxyethane. A suspension of 61 g (1.613 mol) of sodium borohydride in 64 g of 1,2-dimethoxyethane was dropped thereinto at 20° C. or below. The mixture was reacted for 24 hr, and the 1,2-dimethoxyethane was almost completely distilled off from the reaction mixture. 300 g of a 5% aqueous sodium hydroxide solution was added to the residue, thereby separating it into an organic phase and a water phase. The organic phase was again concentrated and filtered to thereby remove impurities. The obtained filtrate was cooled. Thus, 77 g of trihydro(N-methylmethanamine)boron was obtained.

Yield: 85%,

Purity: 99% (measured by iodometry and the hydrogen gas evolution method), and

Melting point: 35° C.

Example 2

60 g (0.628 mol) of trimethylamine hydrochloride was suspended in 94 g of 1,2-dimethoxyethane. A suspension of 25 g (0.661 mol) of sodium borohydride in 26 g of 1,2-dimethoxyethane was dropped thereinto at 20° C. or below. The mixture was reacted for 24 hr, and the 1,2-dimethoxyethane was distilled off from the reaction mixture. 140 g of a 5% aqueous sodium hydroxide solution was added to the residue, thereby separating it into an organic phase and a water phase. The organic phase was filtered to thereby remove impurities, and the obtained filtrate was cooled. Thus, 27 g (59%) of (N,N-dimethylmethanamine) trihydroboron having a purity of 98% was obtained as the first crystal. 80 g of 1,2-dimethoxyethane was distilled off from the filtrate, and the residue was cooled. Thus, 14 g (31%) of (N,N-dimethylmethanamine)trihydroboron having a purity of 98% was obtained as the second crystal.

Yield: 90%,

Purity: 98% (measured by iodometry), and

Melting point: 94° C. (93.5 to 94.5° C., ref.: Inorg. Chem. 1984, 23, 2746–2753).

What is claimed is:

1. A process for producing an amine borane compound of high purity, comprising the steps of:

reacting an amine salt with sodium borohydride in an organic solvent, distilling off the organic solvent to thereby obtain a distillation residue, adding an aqueous alkali hydroxide solution to the distillation residue to thereby form an organic phase and a water phase, fractionating the organic phase, and distilling off the organic solvent from the organic phase.

2. The process as claimed in claim 1, wherein the organic solvent is 1,2-dimethoxyethane.

3. The process as claimed in claim 1, wherein the amine salt is a dimethylammonium salt or a trimethylammonium salt.

4. The process as claimed in claim 1, wherein the aqueous alkali hydroxide solution is an aqueous sodium hydroxide solution having a concentration (normality) of 0.1 to 12 N.

* * * * *